US007358366B2

(12) United States Patent
Blackler et al.

(10) Patent No.: US 7,358,366 B2
(45) Date of Patent: Apr. 15, 2008

(54) THIAZOLIDINEDIONE DERIVATIVE AND ITS USE AS ANTIDIABETIC

(75) Inventors: Paul David James Blackler, Cadiz (ES); Robert Gordon Giles, Tonbridge (GB); Stephen Moore, Tonbridge (GB); Michael John Sasse, Tonbridge (GB)

(73) Assignee: SmithKline Beecham p.l.c., Brentford, Middlesex (GB)

( * ) Notice: Subject to any disclaimer, the term of this patent is extended or adjusted under 35 U.S.C. 154(b) by 0 days.

(21) Appl. No.: 11/458,471

(22) Filed: Jul. 19, 2006

(65) Prior Publication Data

US 2006/0247279 A1    Nov. 2, 2006

Related U.S. Application Data

(63) Continuation of application No. 10/843,741, filed on May 12, 2004, now abandoned, which is a continuation of application No. 10/030,877, filed on Apr. 22, 2002, which is a continuation of application No. PCT/GB00/01522, filed on Apr. 19, 2000, now abandoned.

(30) Foreign Application Priority Data

Apr. 23, 1999  (GB) ................................. 9909471.6
May 25, 1999  (GB) ................................. 9912195.6

(51) Int. Cl.
*C07D 417/12*   (2006.01)
(52) U.S. Cl. ................................. 546/269.7
(58) Field of Classification Search ............. 546/269.7; 514/342
See application file for complete search history.

(56) References Cited

U.S. PATENT DOCUMENTS

| 5,708,012 | A | 1/1998 | Olefsky |
| 5,741,803 | A | 4/1998 | Pool et al. |
| 5,002,953 | A | 3/1999 | Hindley |
| 5,910,592 | A | 6/1999 | Pool et al. |
| 2002/0099081 | A1 | 7/2002 | Sasse et al. |
| 2003/0120078 | A1 | 6/2003 | Sasse et al. |

FOREIGN PATENT DOCUMENTS

| CN | 1277965 | 12/2000 |
| EP | 0306228 B1 | 11/1999 |
| EP | 1468997 A2 | 10/2004 |
| WO | 9310254 | 3/1993 |
| WO | 9405659 | 3/1994 |
| WO | 9521603 | 8/1995 |
| WO | 9855122 | 12/1998 |
| WO | 0031095 | 6/1999 |
| WO | 9931093 | 6/1999 |
| WO | 9931094 | 6/1999 |
| WO | 0064892 | 11/2000 |
| WO | 0064896 | 11/2000 |
| WO | 0226737 | 4/2002 |
| WO | 0462667 | 7/2004 |
| WO | 0485435 | 10/2004 |
| WO | 0521541 | 3/2005 |

OTHER PUBLICATIONS

Brittain, "Polymorphism in Pharmaceutical Solids", NY:Marcel Dekker, Inc 1999, p. 185.*
"A Bioequivalence Study Comparing Tablets Manufactured with the 8 mg Anhydrate Form IV (ANF4) to the Commercial Anhydrate Form I (ANF1) of Rosiglitazone Maleate." Clinical Trial Registry Report for Study No. BRL49653C/300, Oct. 27, 2005. http://ctr.gsk.co.uk/Summary/Rosiglitazone/1_49653_300.pdf.
Phadnis et al. Journal Pharmaceutical and Biomedical Analysis, vol. 15, pp. 929-943 (1997).
Chakravarty et al. International Journal of Pharmaceutics, vol. 288, pp. 335-348 (2005).
Brittain, "Polymorphism in Pharmaceutical Solids", NY:Marcel Dekker, Inc. 1999, pp. 1-2.
Haleblian et al. J. Pharm. Sci., 58(8):911-929 (1969).
Cantello et al. Bioorg. & Med. Chem. Ltr., 4(10):1181-1184 (1994).
Chem. & Engineering News, Feb. 2003, pp. 32-35.
U.S. Pharmacopia #23, National Formulary #18 (1995), pp. 1843-1844.
Muzaffar et al. J. of Pharmacy (Lahore) (1979), 1(1), pp. 59-66.
Jain et al., Indian Drugs, 1986, 23(6): 315-329.
Taday et al. J. Pharmaceutical Sciences, 92(4), Apr. 2003, pp. 831-838.
Concise Encyclopedia, Walter de Gruyter Berline, NY, 1994, pp. 872-873.
Otsuka et al., Chem. Pharm. Bull. 47(6), 852-856 (1999).
Doelker et al., Ann. Pharm. Fr. 2002, 60: 161-176.

* cited by examiner

*Primary Examiner*—Patricia L. Morris
(74) *Attorney, Agent, or Firm*—Kathryn L. Sieburth; Mary E. McCarthy; Charles M. Kinzig

(57) ABSTRACT

A polymorphic form of 5-[4-[2-(N-methyl-N-(2-pyridyl)amino)ethoxy]benzyl]thiazolidine-2,4-dione, maleic acid salt (the "Polymorph") characterised in that it provides: (i) an infra red spectrum containing peaks at 1752, 1546, 1154, 621, and 602 $cm^{-1}$; and/or (ii) a Raman spectrum containing peaks at 1751, 1243 and 602 $cm^{-1}$; and/or (iii) a solid-state nuclear magnetic resonance spectrum containing peaks at 111.9, 114.8, 119.6, 129.2, 134.0, 138.0, 144.7, 153.2, 157.1, 170.7, 172.0, and 175.0 ppm; and/or (iv) an X-ray powder diffraction (XRPD) pattern which gives calculated lattice spacings of 6.46, 5.39, 4.83, 4.68, 3.71, 3.63, 3.58, and 3.48 Angstroms; a process for preparing such a compound, a pharmaceutical composition containing such a compound and the use of such a compound in medicine.

8 Claims, 4 Drawing Sheets

THIAZOLIDINEDIONE DERIVATIVE AND ITS USE AS ANTIDIABETIC

This application is a continuation of U.S. patent application Ser. No. 10/843,741, filed May 12, 2004, abandoned, which is a continuation of U.S. patent application Ser. No. 10/030,877, filed Apr. 22, 2002, abandoned, which is a 371 of International Patent Application No. PCT/GB00/01522, filed Apr. 19, 2000.

This invention relates to a novel pharmaceutical, to a process for the preparation of the pharmaceutical and to the use of the pharmaceutical in medicine.

International Patent Application, Publication Number WO94/05659 discloses certain thiazolidinedione derivatives having hypoglycaemic and hypolipidaemic activity including 5-[4-[2-(N-methyl-N-(2-pyridyl) amino)ethoxy]benzyl]thiazolidine-2,4-dione, maleic acid salt (hereinafter also referred to as "Compound (I)").

International Patent Applications, Publication Numbers WO99/31093, WO99/31094 and WO99/31095 each disclose distinct hydrates of Compound (I).

It has now been discovered that Compound (I) exists in a novel polymorphic form which is particularly suitable for bulk preparation and handling. The novel form can be prepared by an efficient, economic and reproducible process particularly suited to large-scale preparation.

The novel polymorphic form ('the Polymorph') also has useful pharmaceutical properties and in particular it is indicated to be useful for the treatment and/or prophylaxis of diabetes mellitus, conditions associated with diabetes mellitus and certain complications thereof.

Accordingly, the present invention provides a polymorphic form of 5-[4-[2-(N-methyl-N-(2-pyridyl) amino) ethoxy]benzyl]thiazolidine-2,4-dione, maleic acid salt characterised in that it:

(i) provides an infra red spectrum containing peaks at 1752, 1546, 1154, 621, and 602 cm$^{-1}$; and/or
(ii) provides a Raman spectrum containing peaks at 1751, 1243 and 602 cm$^{-1}$; and/or
(iii) provides a solid-state nuclear magnetic resonance spectrum containing peaks at 111.9, 114.8, 119.6, 129.2, 134.0, 138.0, 144.7, 153.2, 157.1, 170.7, 172.0 and 175.0 ppm; and/or
(iv) provides an X-ray powder diffraction (XRPD) pattern which gives calculated lattice spacings of 6.46, 5.39, 4.83, 4.68, 3.71, 3.63, 3.58, and 3.48 Angstroms.

Figure 1:
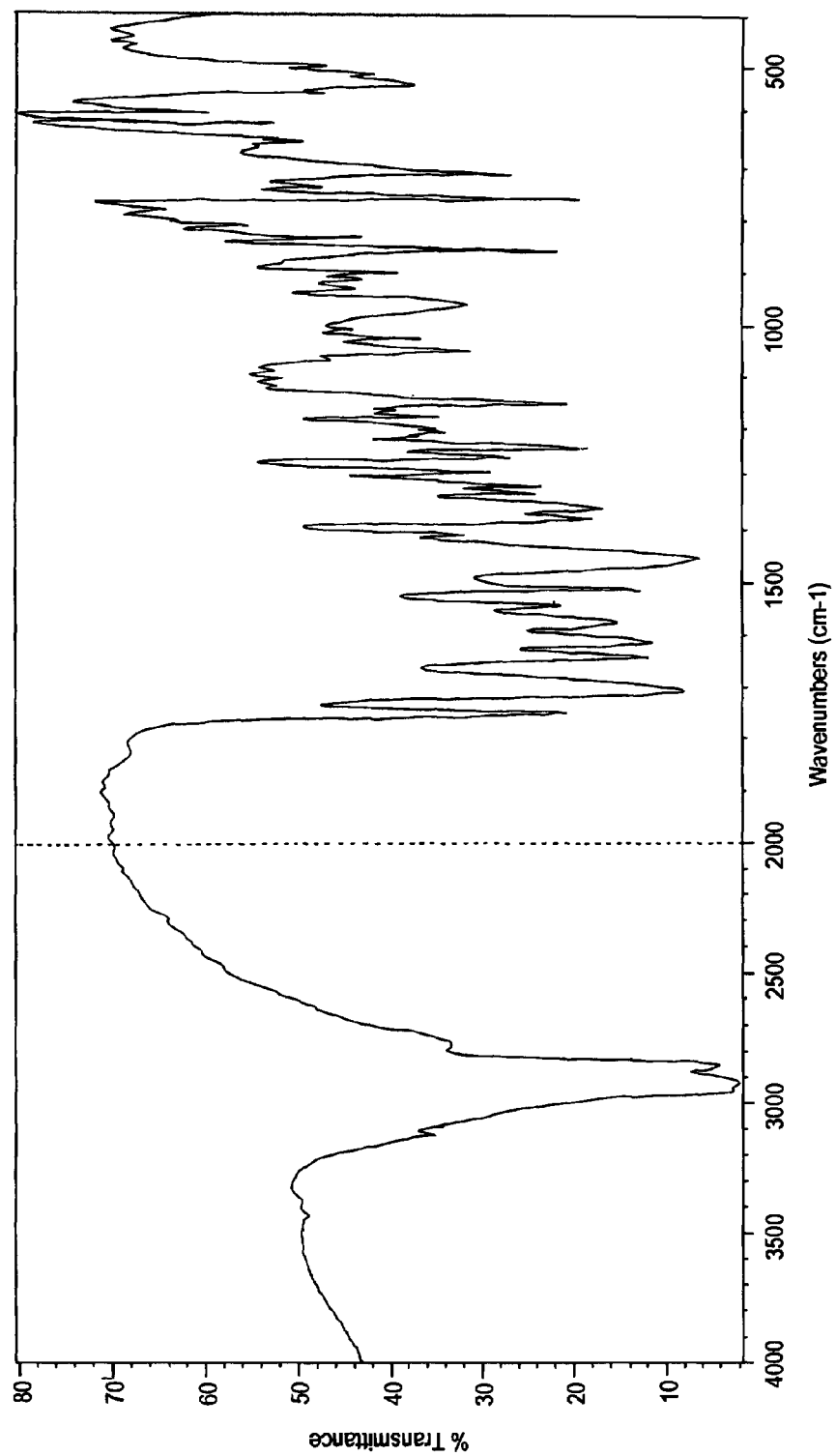
FIG. 1 is the infrared spectrum of the polymorph.

In one favoured aspect, the Polymorph provides an infrared spectrum substantially in accordance with FIG. I.

In one favoured aspect, the Polymorph provides a Raman spectrum substantially in accordance with FIG. II.

In one favoured aspect, the Polymorph provides a solid-state nuclear magnetic resonance spectrum substantially in accordance with FIG. III and/or Table I.

In one favoured aspect, the Polymorph provides an X-ray powder diffraction (XRPD) pattern substantially in accordance with FIG. IV and/or Table II.

The present invention encompasses the Polymorph isolated in pure form or when admixed with other materials, for example the known forms of Compound I or any other material.

Thus in one aspect there is provided the Polymorph in isolated form.

In a further aspect there is provided the Polymorph in pure form.

In yet a further aspect there is provided the Polymorph in crystalline form. The invention also provides a process for preparing the Polymorph, characterised in that a solution of Compound (I) in denatured ethanol at an elevated temperature, preferably in the range of from 65° C. to 70° C. for example 67.5° C., is cooled preferably to a temperature in the range of from 20° C. to 25° C., so as to provide crystallisation of the Polymorph. Preferably, the solution is filtered prior to cooling. In the above-mentioned process the solution may be seeded with the Polymorph to induce crystallisation but this is not essential.

The Polymorph is then recovered from the denatured ethanol. The solution of Compound (I) in the denatured ethanol is conveniently prepared by dissolving Compound (I) in the required amount of denatured ethanol at an elevated temperature, for example 60° C. or 70° C.

Conveniently the Polymorph is recovered from the denatured ethanol by filtration and subsequent drying.

In a further aspect, the invention provides a process for converting Polymorph to Compound (I), wherein a solution of Polymorph in a suitable solvent, such as acetone or ethanol, is seeded with Compound (I); preferably the reaction is carried out in an inert atmosphere, such as nitrogen. Generally, the solution of Polymorph is obtained by dissolving Polymorph at an elevated temperature in the solvent, such as acetone or ethanol.

Compound (I) is prepared according to known procedures, such as those disclosed in WO94/05659. The disclosures of WO94/05659 are incorporated herein by reference For the avoidance of doubt the term "Compound (I)" as used herein refers to the form of 5-[4-[2-(N-methyl-N-(2-pyridyl) amino)ethoxy]benzyl]thiazolidine-2,4-dione, maleic acid salt as disclosed an characterised in International Patent Application, Publication Number WO94/05659.

When used herein "denatured ethanol" means ethanol containing small amounts of methanol, usually up to 5% v/v of methanol, such as from 0.9% v/v to 5% v/v of methanol, for example ethanol containing 4% v/v of methanol.

When used herein the term 'prophylaxis of conditions associated with diabetes mellitus' includes the treatment of conditions such as insulin resistance, impaired glucose tolerance, hyperinsulinaemia and gestational diabetes.

Diabetes mellitus preferably means Type II diabetes mellitus.

Conditions associated with diabetes include hyperglycaemia and insulin resistance and obesity. Further conditions associated with diabetes include hypertension, cardiovascular disease, especially atherosclerosis, certain eating disorders, in particular the regulation of appetite and food intake in subjects suffering from disorders associated with under-eating, such as anorexia nervosa, and disorders associated with over-eating, such as obesity and anorexia bulimia. Additional conditions associated with diabetes include polycystic ovarian syndrome and steroid induced insulin resistance.

The complications of conditions associated with diabetes mellitus encompassed herein includes renal disease, especially renal disease associated with the development of Type II diabetes including diabetic nephropathy, glomerulonephritis, glomerular sclerosis, nephrotic syndrome, hypertensive nephrosclerosis and end stage renal disease.

As mentioned above the compound of the invention has useful therapeutic properties: The present invention accordingly the Polymorph for use as an active therapeutic substance.

More particularly, the present invention provides the Polymorph for use in the treatment and/or prophylaxis of diabetes mellitus, conditions associated with diabetes mellitus and certain complications thereof.

The Polymorph may be administered per se or, preferably, as a pharmaceutical composition also comprising a pharmaceutically acceptable carrier. The formulation of the Polymorph and dosages thereof are generally as disclosed for Compound (I) in International Patent Application, Publication Number WO94/05659 or WO98/55122.

Accordingly, the present invention also provides a pharmaceutical composition comprising the Polymorph and a pharmaceutically acceptable carrier therefor.

The Polymorph is normally administered in unit dosage form.

The active compound may be administered by any suitable route but usually by the oral or parenteral routes. For such use, the compound will normally be employed in the form of a pharmaceutical composition in association with a pharmaceutical carrier, diluent and/or excipient, although the exact form of the composition will naturally depend on the mode of administration.

Compositions are prepared by admixture and are suitably adapted for oral, parenteral or topical administration, and as such may be in the form of tablets, capsules, oral liquid preparations, powders, granules, lozenges, pastilles, reconstitutable powders, injectable and infusable solutions or suspensions, suppositories and transdermal devices. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

Solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the active compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the active compound is suspended in the vehicle instead of being dissolved and sterilised by exposure to ethylene oxide before suspending in the sterile vehicle. Advantageously, a surfactant or wetting agent is included in the composition to facilitate uniform distribution of the active compound.

In addition such compositions may contain further active agents such as anti-hypertensive agents and diuretics.

In addition, the Polymorph may be used in combination with other antidiabetic agents such as insulin secretagogues, for example sulphonylureas, biguanides, such as metformin, alpha glucosidase inhibitors, such as acarbose, beta agonists, and insulin such as those disclosed in WO98/57649, WO98/57634, WO98/57635 or WO98/57636. The other antidiabetic agents, the amounts thereof and methods of administration are as described in the above mentioned publications. The formulation of the Polymorph and dosages thereof in said combinations are generally as disclosed for Compound (I) in the above mentioned publications. As is common practice, the compositions will usually be accompanied by written or printed directions for use in the medical treatment concerned.

As used herein the term 'pharmaceutically acceptable' embraces compounds, compositions and ingredients for both human and veterinary use: for example the term 'pharmaceutically acceptable salt' embraces a veterinarily acceptable salt.

The present invention further provides a method for the treatment and/or prophylaxis of diabetes mellitus, conditions associated with diabetes mellitus and certain complications thereof, in a human or non-human mammal which comprises administering an effective, non-toxic, amount of the Polymorph to a human or non-human mammal in need thereof.

Conveniently, the active ingredient may be administered as a pharmaceutical composition hereinbefore defined, and this forms a particular aspect of the present invention.

In the treatment and/or prophylaxis of diabetes mellitus, conditions associated with diabetes mellitus and certain complications thereof the Polymorph may be taken in doses, such as those described above.

Similar dosage regimens are suitable for the treatment and/or prophylaxis of non-human mammals.

In a further aspect the present invention provides the use of the Polymorph for the manufacture of a medicament for the treatment and/or prophylaxis of diabetes mellitus, conditions associated with diabetes mellitus and certain complications thereof.

No adverse toxicological effects are indicated in the above mentioned treatments for the compounds of the invention.

The following example illustrates the invention but do not limit it in any way.

EXAMPLE 1

Preparation of the Polymorph

A mixture of maleic acid (2.10 g) and 5-[4-[2-(N-methyl-N-(2-pyridyl) amino)ethoxy]benzyl] thiazolidine-2,4-dione (6.0 g) were heated to 70° C. in denatured ethanol (60 ml, 5% v/v methanol) until complete dissolution was obtained. The resultant solution was filtered, re-heated to 67.5° C., and then cooled to 20-25° C. The resulting crystalline product was filtered off, washed with denatured ethanol (10 ml) and dried at 50° C. in vacuo to give the Polymorph_(6.61 g, 83%).

EXAMPLE 2

Conversion of Polymorph to Compound (1)

Polymorph (10.0 g) was added to denatured ethanol (90 ml) under nitrogen. The resulting mixture was stirred and heated to 68° C., and held at this temperature for 30 min. The solution was hot filtered to a preheated vessel (56° C.) and the filter washed with hot denatured ethanol (10 ml). The temperature of the filtrate was adjusted to 60° C. and then cooled with stirring. At 55° C. the solution was seeded with Compound (I) (0.4 g) and cooling, with stirring, continued. The resulting slurry was stirred at ambient temperature for 1 h, and the solid isolated by filtration, washed with denatured ethanol and dried at 50° C. in vacuo to give 8.4 g (84%) Compound (I).

EXAMPLE 3

Conversion of Polymorph to Compound (1)

Polymorph (5.0 g) was added to acetone (170 ml) and the mixture was stirred and heated to reflux temperature. After complete dissolution, the solution was heated at reflux for 30 min, then filtered. The filtered solution was concentrated by distillation at atmospheric pressure (120 ml of distillate was collected). The remaining solution was stirred and cooled at about 1° C./min and at 50° C. seeded with Compound (I) (0.2 g). Cooling was continued at 1° C./min, and when the slurry reached 20° C. stirring was continued for 1 h. The solid was isolated by filtration, washed with acetone and dried in vacuo at 50° C. to give 4.2 g (84%) of Compound (I).

CHARACTERISING DATA: The following characterising data were generated for the polymorph:

A Infrared

The infrared absorption spectrum of a mineral oil dispersion of the Polymorph was obtained using a Nicolet 710 FT-IR spectrometer at 2 cm$^{-1}$ resolution. Data were digitised at 1 cm$^{-1}$ intervals. The spectrum obtained is shown in FIG. I. Peak positions are as follows 1752, 1709, 1642, 1613, 1576, 1546, 1514, 1412, 1359, 1329, 1317, 1291, 1261, 1242, 1220, 1212, 1204, 1182, 1171, 1154, 1126, 1112, 1097, 1075, 1056, 1032, 1016, 966, 937, 918, 906, 861, 842, 821, 809, 792, 762, 743, 715, 665, 656, 650, 621, 602, 560, 541, 524 and 507 cm$^{-1}$.

B Raman

The Raman spectrum of the Polymorph was recorded through a glass vial using a Perkin Elmer 2000R spectrometer at 4 cm$^{-1}$ resolution and is shown in FIG. II (X-axis shows Intensity, Y-axis shows Raman shift cm$^{-1}$, 1800-200 cm$^{-1}$). Excitation was achieved using a Nd:YAG laser (1064 nm) with a power output of 400 mW. Peak positions are as follows: 1751, 1683, 1614, 1586, 1547, 1468, 1449, 1382, 1344, 1317, 1243, 1211, 1181, 1150, 1076, 1016, 991, 918, 841, 825, 773, 742, 652, 637, 619, 602, 512, 470, 428, 406, 350 and 325 cm$^{-1}$.

C NMR

The 90.56 MHz $^{13}$C CP-MAS NMR spectrum for the Polymorph is shown in FIG. III. Chemical shifts are tabulated in Table 1. Data were recorded at ambient temperature and 10 kHz spinning frequency on a Bruker AMX360 spectrometer, with 1.6 ms cross polarization, and a repetition time of 15 s. Chemical shifts were externally referenced to the carboxylate signal of a glycine test sample at 176.4 ppm relative to tetramethylsilane, and are regarded as accurate to within +/− 0.5 ppm.

TABLE I $^{13}$C Chemical Shifts of the Polymorph.
Chemical Shift (ppm)

| | | | | |
|---|---|---|---|---|
| 38.0 | 62.8 | 129.2 | 153.2 | 175.0 |
| 49.4 | 111.9 | 134.0 | 157.1 | |
| 51.9 | 114.8 | 138.0 | 170.7 | |
| 57.6 | 119.6 | 144.7 | 172.0 | |

D X-Ray Powder Diffraction (XRPD)

The XRPD pattern of the Polymorph is shown below in FIG. IV and a summary of the XRPD angles and calculated lattice spacings characteristic of the Polymorph is given in Table II.

Data were acquired on a Bruker D8 Advance X-ray diffractometer with theta/theta geometry configured with a Cu anode, primary and secondary Soller slits, a secondary monochromator, and scintillation detector. The following acquisition conditions were used:

| | |
|---|---|
| Tube anode: | Cu |
| Generator tension: | 40 kV |
| Generator current: | 40 mA |
| Start angle: | 2.0 °2θ |
| End angle: | 35.0 °2θ |
| Step size: | 0.02 °2θ |
| Time per step: | 2.5 s |

TABLE II

X-Ray Powder Diffraction Angles and Calculated Lattice Spacings Characteristic of the Polymorph.

| Diffraction Angle (°2θ) | Lattice Spacing (Angstroms) |
|---|---|
| 9.2 | 9.63 |
| 11.6 | 7.65 |
| 12.3 | 7.17 |
| 13.7 | 6.46 |
| 14.0 | 6.32 |
| 14.7 | 6.03 |
| 14.9 | 5.95 |
| 15.3 | 5.77 |
| 16.4 | 5.39 |

TABLE II-continued

X-Ray Powder Diffraction Angles and Calculated Lattice Spacings Characteristic of the Polymorph.

| Diffraction Angle (°2θ) | Lattice Spacing (Angstroms) |
|---|---|
| 18.4 | 4.83 |
| 18.7 | 4.74 |
| 19.0 | 4.68 |
| 19.3 | 4.59 |
| 20.0 | 4.44 |
| 21.0 | 4.22 |
| 21.9 | 4.07 |
| 22.5 | 3.94 |
| 23.3 | 3.81 |
| 24.0 | 3.71 |
| 24.5 | 3.63 |
| 24.9 | 3.58 |
| 25.6 | 3.48 |
| 26.2 | 3.40 |
| 27.2 | 3.28 |
| 27.7 | 3.22 |
| 28.7 | 3.11 |
| 29.2 | 3.05 |
| 29.6 | 3.02 |
| 30.2 | 2.96 |
| 30.8 | 2.90 |
| 31.0 | 2.88 |
| 31.7 | 2.82 |
| 32.3 | 2.77 |
| 32.9 | 2.72 |
| 33.4 | 2.68 |
| 34.2 | 2.62 |

The invention claimed is:

1. A crystalline 5-[4-[2-(N-methyl-N-(2-pyridyl)amino) ethoxy]benzyl]thiazolidine-2,4-dione maleic acid salt which provides at least one of:
    (i) an infra red spectrum containing peaks at 1752, 1546, 1154, 621, and 602 cm$^{-1}$;
    (ii) a Raman spectrum containing peaks at 1751, 1243 and 602 cm$^{-1}$;
    (iii) a solid-state $^{13}$C nuclear magnetic resonance spectrum containing peaks at 111.9, 114.8, 119.6, 129.2, 134.0, 138.0, 144.7, 153.2, 157.1, 170.7, 172.0 and 175.0 ppm; and
    (iv) an X-ray powder diffraction pattern which gives calculated lattice spacings of 6.46, 5.39, 4.83, 4.68, 3.71, 3.63, 3.58, and 3.48 Angstroms.

2. A crystalline 5-[4-[2-(N-methyl-N-(2-pyridyl) amino) ethoxy]benzyl]thiazolidine-2,4-dione maleic acid salt which provides each of:
    (i) an infra red spectrum containing peaks at 1752, 1546, 1154, 621, and 602 cm$^{-1}$;
    (ii) a Raman spectrum containing peaks at 1751, 1243 and 602 cm$^{-1}$;
    (iii) a solid-state $^{13}$C nuclear magnetic resonance spectrum containing peaks at 111.9, 114.8, 119.6, 129.2, 134.0, 138.0, 144.7, 153.2, 157.1, 170.7, 172.0 and 175.0 ppm; and
    (iv) an X-ray powder diffraction pattern which gives calculated lattice spacings of 6.46, 5.39, 4.83, 4.68, 3.71, 3.63, 3.58, and 3.48 Angstroms.

3. A crystalline 5-[4-[2-(N-methyl-N-(2-pyridyl) amino) ethoxy]benzyl]thiazolidine-2,4-dione maleic acid salt, which, in a mineral oil dispersion, provides an infra red spectrum substantially in accordance with FIG. 1.

Figure 2:
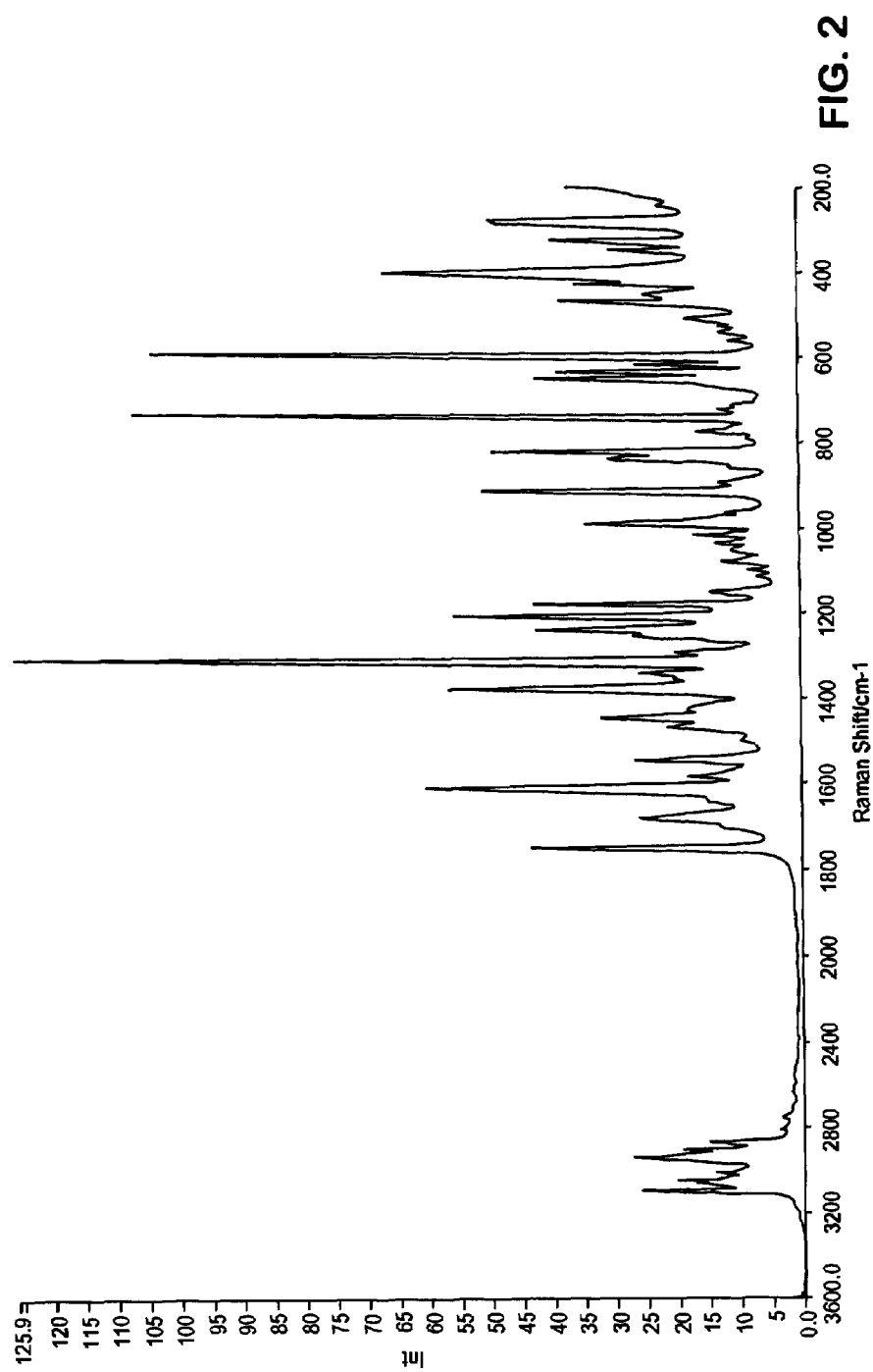
FIG. 2 is the Raman spectrum of the polymorph.

4. A crystalline 5-[4-[2-(N-methyl-N-(2-pyridyl)amino) ethoxy]benzyl]thiazolidine-2,4-dione maleic acid salt, which provides a Raman spectrum substantially in accordance with FIG. 2.

Figure 3:
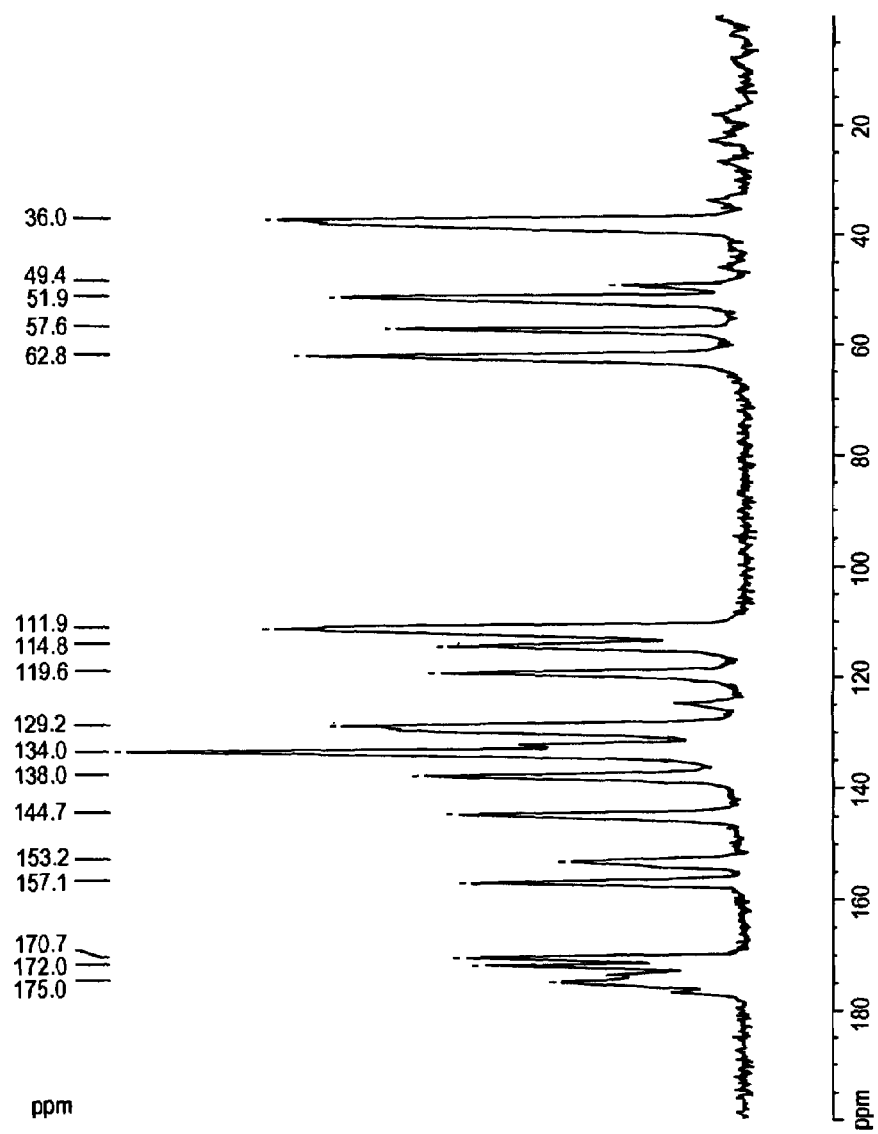
FIG. 3 is the solid state NMR spectrum of the polymorph.

5. A crystalline 5-[4-[2-(N-methyl-N-(2-pyridyl)amino) ethoxy]benzyl]thiazolidine-2,4-dione maleic acid salt, which provides a solid-state $^{13}$C nuclear magnetic resonance spectrum substantially in accordance with FIG. 3.

Figure 4:
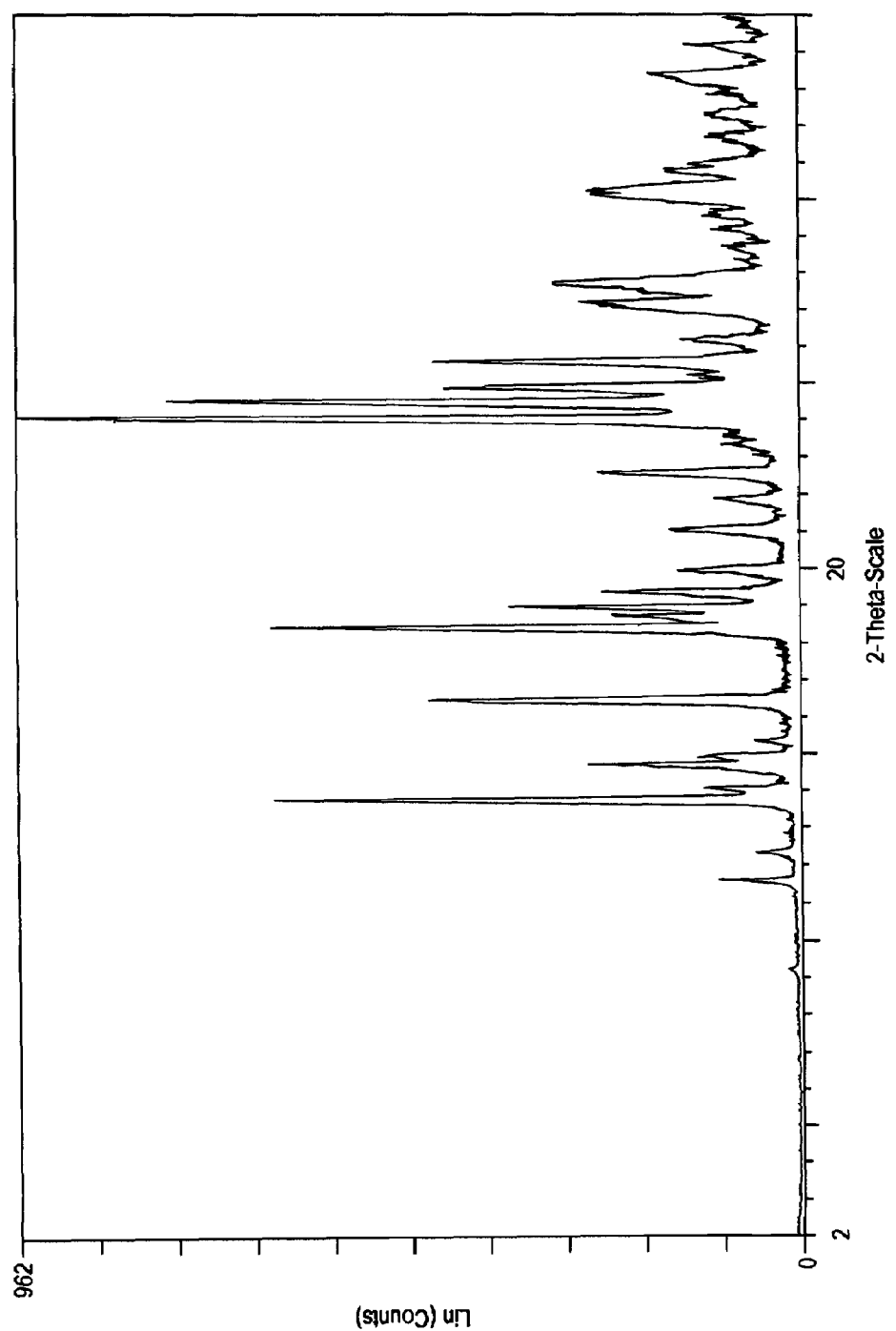
FIG. 4 is the X-ray powder diffraction pattern of the polymorph.

6. A crystalline 5-[4-[2-(N-methyl-N-(2-pyridyl)amino) ethoxy]benzyl]thiazolidine-2,4-dione, maleic acid salt, which provides an X-ray powder diffraction pattern substantially in accordance with FIG. 4.

7. A crystalline 5-[4-[2-(N-methyl-N-(2-pyridyl)amino) ethoxy]benzyl]thiazolidine-2,4-dione maleic acid salt, which provides a solid-state $^{13}$C nuclear magnetic resonance spectrum having absorbances at 38.0, 49.4, 51.9, 57.6, 62.8, 111.9, 114.8, 119.6, 129.2, 134.0, 138.0, 144.7, 153.2, 157.1, 170.7, 172.0, 175.0 +/− 0.5 ppm.

8. A crystalline 5-[4-[2-(N-methyl-N-(2-pyridyl)amino) ethoxy]benzyl]thiazolidine-2,4-dione maleic acid salt, which provides an X-ray powder diffraction pattern having peaks with diffraction angles and calculated lattice spacings as follows:

| Diffraction Angles (°2θ) | Lattice Spacings (Angstroms) |
|---|---|
| 9.2 | 9.63 |
| 11.6 | 7.65 |
| 12.3 | 7.17 |
| 13.7 | 6.46 |
| 14.0 | 6.32 |
| 14.7 | 6.03 |
| 14.9 | 5.95 |
| 15.3 | 5.77 |
| 16.4 | 5.39 |
| 18.4 | 4.83 |
| 18.7 | 4.74 |
| 19.0 | 4.68 |
| 19.3 | 4.59 |
| 20.0 | 4.44 |
| 21.0 | 4.22 |
| 21.9 | 4.07 |
| 22.5 | 3.94 |
| 23.3 | 3.81 |
| 24.0 | 3.71 |
| 24.5 | 3.63 |
| 24.9 | 3.58 |
| 25.6 | 3.48 |
| 26.2 | 3.40 |
| 27.2 | 3.28 |
| 27.7 | 3.22 |
| 28.7 | 3.11 |
| 29.2 | 3.05 |
| 29.6 | 3.02 |
| 30.2 | 2.96 |
| 30.8 | 2.90 |
| 31.0 | 2.88 |
| 31.7 | 2.82 |
| 32.3 | 2.77 |
| 32.9 | 2.72 |
| 33.4 | 2.68 |
| 34.2 | 2.62. |

* * * * *